US009830732B1

(12) United States Patent
Punjani et al.

(10) Patent No.: US 9,830,732 B1
(45) Date of Patent: Nov. 28, 2017

(54) METHODS AND SYSTEMS FOR IMAGE ALIGNMENT OF AT LEAST ONE IMAGE TO A MODEL

(71) Applicant: THE GOVERNING COUNCIL OF THE UNIVERSITY OF TORONTO, Toronto (CA)

(72) Inventors: Ali Punjani, Toronto (CA); Marcus Anthony Brubaker, Toronto (CA); David James Fleet, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 15/596,173

(22) Filed: May 16, 2017

Related U.S. Application Data

(60) Provisional application No. 62/336,831, filed on May 16, 2016.

(51) Int. Cl.
G06T 15/04 (2011.01)
G06T 19/20 (2011.01)

(52) U.S. Cl.
CPC .............. G06T 15/04 (2013.01); G06T 19/20 (2013.01)

(58) Field of Classification Search
None
See application file for complete search history.

(56) References Cited

U.S. PATENT DOCUMENTS

2012/0133779 A1* 5/2012 Ma .................... G06K 9/6249
348/175

2014/0270425 A1* 9/2014 Kenny ................. G06T 7/0012
382/128

OTHER PUBLICATIONS

Peng, Xiaoming, et al. "A practical two-step image registration method for two-dimensional images." Information Fusion 5.4 (2004): 283-298.*
Mount, David M., Nathan S. Netanyahu, and Jacqueline Le Moigne. "Efficient algorithms for robust feature matching." Pattern recognition 32.1 (1999): 17-38.*
Little, J.D.C., Karel, C., Murty, K.G. & Sweeney, D.W. An algorithm for the traveling salesman problem. Oper. Res. 11, 972-989 (1963).
Yang, J., Li, H. & Jia, Y. Go-ICP: Solving 3D Registration Efficiently and Globally Optimally. In Proc. IEEE Int. Conf. Comput. Vis. (eds. Davis, L. & Hartley, R.) 1457-1464 (IEEE, 2013).
Scheres, S.H.W (2012) Journal of Molecular Biology, 415:406-418 entitled a Bayesian View on Cryo-EM Structure Determination.
Grigorieff, N. (2007) Journal of Structural Biology, 157:117-125 entitled Frealign: High-resolution refinement of single particle structures.
International Search Report corresponding to PCT/CA2017/050591; Canadian Intellectual Property Office; dated Aug. 31, 2017.

(Continued)

*Primary Examiner* — Yi Wang
(74) *Attorney, Agent, or Firm* — Bhole IP Law; Anil Bhole

(57) ABSTRACT

A system and a method for image alignment between at least two images to a three-dimensional model. The method including: determining a lower bound and an upper bound of an acceptable likelihood of mismatch between the at least two images; evaluating the likelihood of mismatch between the at least two images over a set of poses (r), shifts (t), or both poses (r) and shifts (t); and discarding those evaluations resulting beyond the lower bound and upper bound.

14 Claims, 22 Drawing Sheets

(56) References Cited

OTHER PUBLICATIONS

Written Opinion corresponding to PCT/CA2017/050591; Canadian Intellectual Property Office; dated Aug. 31, 2017.
Punjani et al., "Building Proteins in a Day: Efficient 3D Molecular Structure Estimation with Electron Cryomicroscopy", Journal of LATEX Class Files, vol. 6, No. 1, Jan. 2007.
Rubinstein et al, "Alignment of cryo-EM movies of individual particles by global optimization of image translations", Journal of Structural Biology, Nov. 30, 2015 (192(2):188-95.
Cheng et al., "A Primer to Single-Particle Cryo-Electron Microscopy", Cell, Apr. 23, 2015, 161(3):438-49.

\* cited by examiner

METHODS AND SYSTEMS FOR IMAGE ALIGNMENT OF AT LEAST ONE IMAGE TO A MODEL

TECHNICAL FIELD

The following relates generally to image alignment and more particularly to aligning images that share a characteristic using an interative process.

SUMMARY

In one aspect, a method for image alignment of at least one two-dimensional or three-dimensional image to a two-dimensional or three-dimensional model is provided, the method executed on a processing unit, the image alignment having an acceptable likelihood of mismatch between the at least one image and the model, the method comprising: selecting a value for a radius in Fourier space; discretizing a set of poses into a discrete grid of candidate poses and a set of shifts into a discrete grid of candidate shifts; determining a fixed fraction (f_keep) as an upper bound on the acceptable likelihood of mismatch, the fixed fraction being determined based on, at least, the fraction of poses and shifts that are discarded on typical dataset of images; determining whether a selected accuracy of image alignment has been obtained, when such determination is false: using the upper bound and a lower bound on the acceptable likelihood of mismatch, the lower bound being a combination of a first component (U(r,t)) and a second component (V(r,t)); determining values for the first component for each of the poses and shifts on the discrete grid of candidate poses and the discrete grid of shifts, using only portions of the image below the selected value for the radius in Fourier space; determining a reference first component (U^*) using the value for the fixed fraction; for every pose in the discrete grid of candidate poses, determining whether the minimum value of the first component over all the candidate shifts is greater than the reference first component and discarding the pose from the discrete grid in such case; for every shift in the discrete grid of candidate shifts, determining whether the minimum value of the first component over all candidate poses is greater than the reference first component and discarding the shift from the discrete grid in such case; for every remaining pose in the discrete grid of candidate poses, replacing the pose with a plurality of subdivided grid points representing the candidate poses; for every remaining shift in the discrete grid of candidate shifts, replacing the shift with a plurality of subdivided grid points representing the candidate shifts; and increasing the radius in the Fourier space; and otherwise, returning the pose and shift at the lower bound with minimum value.

In a particular case, the lower bound is determined with the images at a resolution that is less than the maximum resolution for the images.

In a particular case, the first component is the squared error of Fourier coefficients at or below a selected radius in Fourier space, and the second component is the squared error of Fourier coefficients above the selected radius.

In a particular case, the second component comprises a first subcomponent added to a second subcomponent and subtracted by a third subcomponent, the first subcomponent is the power of one of the images at high frequencies, the second subcomponent is the power of an image of a slice of the three-dimensional model for one of the poses at high frequencies, the third subcomponent is the correlation between the power of each of the images at high frequencies and the power of the image of the slice of the three-dimensional model for one of the poses at high frequencies.

In a particular case, the second subcomponent comprises: $V_1 - \Sigma_{\|l\|>L} \frac{1}{2} C_l^2 |\hat{Y}_l|^2 - $ $$\sqrt[4]{\sum_{\|l\|>L} \frac{1}{2} C_l^2 |\hat{Y}_l|^2},$$

wherein V1 is the power of one of the images at high frequencies, subscript l denotes a wavevector, subscript L denotes the selected radius in the Fourier space, C is a contrast transfer function (CTF) of the image-capturing apparatus, and Y is a vector representing a projection of the three-dimensional model.

In a particular case, the second subcomponent is only recomputed if the CTF of the image-capturing apparatus is different.

In a particular case, the determination of the upper bound comprises evaluating a value for the likelihood of mismatch at a specific pose, specific shift, or both.

In a particular case, determining the reference first component (U*) comprises determining the reference first component (U*) such that:

$$\frac{|\{(r, t); U(r, t) \leq U^*\}|}{|\{(r, t); U(r, t) > U^*\}|} = f_{keep}.$$

In a particular case, the at least one image is two-dimensional and the model is three-dimensional, wherein replacing the pose with the plurality of subdivided grid points comprises replacing the pose with eight subdivided grid points, and replacing the shift with the plurality of subdivided grid points comprises replacing the shift with four subdivided grid points.

In a particular case, the at least one image is two-dimensional and the model is two-dimensional, wherein replacing the pose with the plurality of subdivided grid points comprises replacing the pose with two subdivided grid points, and replacing the shift with the plurality of subdivided grid points comprises replacing the shift with four subdivided grid points.

In a particular case, the at least one image is three-dimensional and the model is three-dimensional, wherein replacing the pose with the plurality of subdivided grid points comprises replacing the pose with eight subdivided grid points, and replacing the shift with the plurality of subdivided grid points comprises replacing the shift with eight subdivided grid points.

In a particular case, the selected accuracy of image alignment is obtained when the value for the radius in Fourier space is equal to the Nyquist rate.

In a particular case, the selected accuracy of image alignment is obtained when a selected number of iterations have been performed.

In a particular case, the fixed fraction ($f_{keep}$) is between 3% and 10%.

In a particular case, the fixed fraction ($f_{keep}$) is approximately 5%.

DESCRIPTION OF THE DRAWINGS

The features of the invention will become more apparent in the following detailed description in which reference is made to the appended drawings wherein.

DETAILED DESCRIPTION

Figure 1:
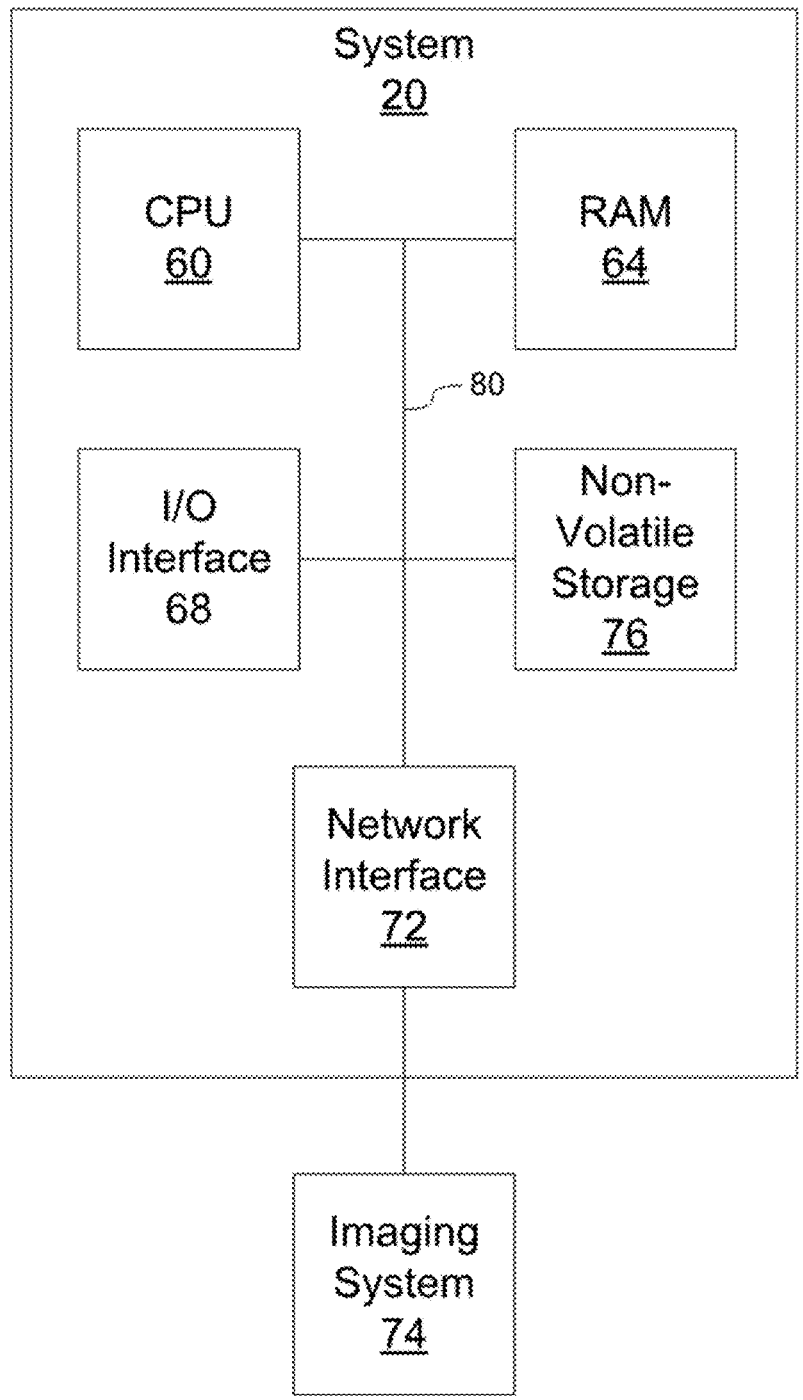
FIG. 1 is a system for image alignment in accordance with an embodiment.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Image alignment challenges occur in several fields of use. As an example, in Single Particle Electron Cryomicroscopy (Cryo-EM), scientists aim to discover the structure and function of important biological macromolecules (proteins, viruses, complexes, etc) by computing 3D atomic structures from a large set of noisy 2D electron micrograph images of the target molecule. Cryo-EM has the potential to unveil the molecular and chemical nature of fundamental biology through the discovery of atomic structures of previously unknown biological structures, many of which have proven difficult or impossible to study by conventional structural biology techniques. As such, Cryo-EM is receiving considerable attention in the life science and structural biology fields. Unfortunately, progress in employing Cryo-EM to study biology widely is hindered by the difficulty of the associated computational task. Today, biologists consider computational expense, in terms of both cost for compute infrastructure and more importantly time wasted waiting for computation, to be a key bottleneck in the Cryo-EM pipeline. Current state-of-the-art methods require weeks or even months of compute time on large clusters with several thousands of cores. In contrast, cryo-imaging of a specimen can currently be done within 48 hours.

The power of cryo-EM to resolve the structures of complex proteins depends entirely on the power of techniques underlying the reconstruction process. Once a good quality signal can be recorded in the microscope, the rest of the burden to actually find a structure comes down to the techniques for processing resulting images. This is especially true as cryo-EM is increasingly applied to more and more difficult-to-purify proteins and heterogeneous samples where many of the collected microscope images do not actually contain the target particle. It is common to see collected datasets with as little as 10 or 20 percent true particles. This high outlier rate is further exacerbated by auto-picking procedures which aim to automate the manual process of finding particles in microscope images. For these reasons, it is clear that the technique for separating true particle images from false ones is critical to reliably discovering new structures, and also in making the process scalable and routine.

Reconstruction of a structure in Cryo-EM is generally considered to be expensive. In the Cryo-EM imaging process, each observed image represents a view of the target 3D structure that it is desired to recover. Crucially, each image comes from an unknown viewing direction. In modern approaches, this pose ambiguity is dealt with by formulating the reconstruction problem as an optimization problem over the space of 3D structures. The objective is to maximize the likelihood (or similar measure) of the structure, given the observed images. The pose variables are treated as nuisance (i.e., latent) variables. As such, computing the optimization objective neccesitates a search problem, known as alignment. In this search problem, which must be carried out for each observed image, the latent pose variables are estimated by searching for the 3D pose and 2D in-plane shift of the 3D structure that best explains the observed image. In some approaches, this search is done implicitly by marginalizing over the pose variable, but this still requires finding the (multitude of) poses for which a particular image aligns well.

$E(r,t)$ is used to denote the alignment error of an image to a 3D structure that has been rotated to the pose r (3D) and translated in-plane by shift t (2D). Alignment, or the minimization of $E(r,t)$, is expensive in current methods because it is solved using exhaustive search over all poses and shifts. Persons of skill in the art are aware that misalignment of images can lead to incorrect 3D structures, and so are keen to ensure that no poses are missed during alignment. When attempting to align images so that atomic resolution structure can be reconstructed, the five dimensional search space must be finely discretized, increasing computational burden further still. Some methods apply ad-hoc measures to cut down on computational cost; these are usually referred to as local searches. Current local search methods come in many flavors, all being ad-hoc and giving no guarantee of finding the correct alignment. Some are based on limiting searches to the region of a previously determined orientation. Others use the concept of coarse-to-fine search, where an alignment is first computed over a coarse grid of possible poses, and subsequently subsampled on finer grids. Local searches are used in practice but only cautiously, as they can introduce alignment inaccuracies and have no guarantees. They can also have tuning parameters that can be difficult to set, as there is no mathematical backing for the ad-hoc procedures.

Disclosed herein are methods and systems for image alignment. The methods and systems described herein are generally applicable to any set of images sharing a characteristic, a specific example of which is Cryo-EM images, for which alignment is desired between various 2D images representing specific poses of a 3D specimen. Other examples of 2D/3D image alignment have imaging examples deriving from microscopes, telescopes, NMR, CT scanners, and MRI. Further examples include those for which 2D/2D and 3D/3D image alignment, symmetry detection or sub-tomography is suitable.

The method comprises defining an upper bound and a lower bound delimiting an acceptable likelihood of mismatch between two given images. In the specific example of Cryo-EM, images are compared to each of a set of expected images of a protein structure at a set of poses and shifts spaced apart at a first coarseness to determine a likelihood of a mismatch between the image and the expected image. The poses and shifts at which the expected images have likelihoods that exceed an upper bound are discarded. The process is repeated for a second set of poses and shifts around the first set of poses and shifts corresponding to un-discarded ones of the expected images, the second set of poses and shifts having a second coarseness that is more fine than the first coarseness. The process is further repeated in further iterations, with sets of poses and shifts becoming successively finer, while determining likelihoods of mismatch at each iteration and discarding successively more poses and shifts, until a suitable termination criterion is reached. The best of the remaining poses and shifts is considered the correct alignment of the image to the reference.

FIG. 1 shows various physical components of a system 20 for image alignment. As will be appreciated, while the system 20 is illustrated as being a single physical computer, it can alternatively be two or more computers acting cooperatively to provide the functionality described. As shown, the system 20 has a number of physical and logical components, including a central processing unit ("CPU") 60, random access memory ("RAM") 64, an input/output ("I/O") interface 68, a network interface 72, non-volatile storage 76, and a local bus 80 enabling the CPU 60 to communicate with the other components. The CPU 60 executes an operating system and an application for performing image alignment. The functionality of an application of the image alignment method is described below in greater detail. The RAM 64 provides relatively responsive volatile storage to the CPU 60. The I/O interface 68 enables an administrator to interact with the system 20 via a keyboard, a mouse, a speaker, and a display. The network interface 72 permits wired or wireless communication with other systems. The non-volatile storage 76 stores computer readable instructions for implementing the operating system and the application for performing image alignment, as well as any data used by the application. During operation of the system 20, the computer readable instructions for the operating system and the application, and the data may be retrieved from the non-volatile storage 76 and placed in the RAM 64 to facilitate execution. An imaging system 74 may further be linked to the system to obtain images for alignment. The imaging system comprise electron microscopes, microscopes, telescopes, NMR, CT scanners, and MRI or other suitable device.

The system 20 executes a general optimization technique known as branch and bound ("BnB") optimization. BnB optimization provides global optimality guarantees and, when executed well, can lead to significant reductions in processing time. BnB operates generally as follows. When searching for the minimum of some objective function, the search space is subdivided (branch) and a method is determined for inexpensively discarding (bound) regions of the search space that cannot possibly contain the minimum. The bound step of BnB requires both an upper and lower bound on the objective function, and typically finding a method for computing a useful lower bound is the most difficult. The bound, given a search region, is designed to determine whether a specified region could possibly contain the minimum, and if not then the region as a whole can be discarded. A powerful and useful lower bound has two qualities: inexpensive computational requirements, since the evaluation is conducted many times, and that the evaluation results in many discarded regions, meaning that the bound is tight and actually provides useful information.

In the present system and method, a set of bounds for image alignment indicate, in a principled way, how poorly or well a given image can align to a given 3D map over a range of poses and shifts, without having to actually evaluate the exact fit error at those poses and shifts. This allows entire regions of pose and shift search space to be discarded using only inexpensive calculations, and allows the best pose to be found efficiently.

The problem of recovering a 3D cryo-EM structure of a molecule from a set of 2D images taken in a microscope is difficult for several reasons, key amongst them the presence of unobserved latent variables like pose and translational shift of the molecule in each image, a problem referred to as the latent variable estimation problem. A person of skill will appreciate the details of various techniques that can solve a latent variable problem, most of which comprise an iterative procedure whereby the current guess of the 3D structure is used to estimate the latent variables (pose, shift), and then these estimates are used to construct a new 'refined' guess of the 3D structure.

Figure 2:
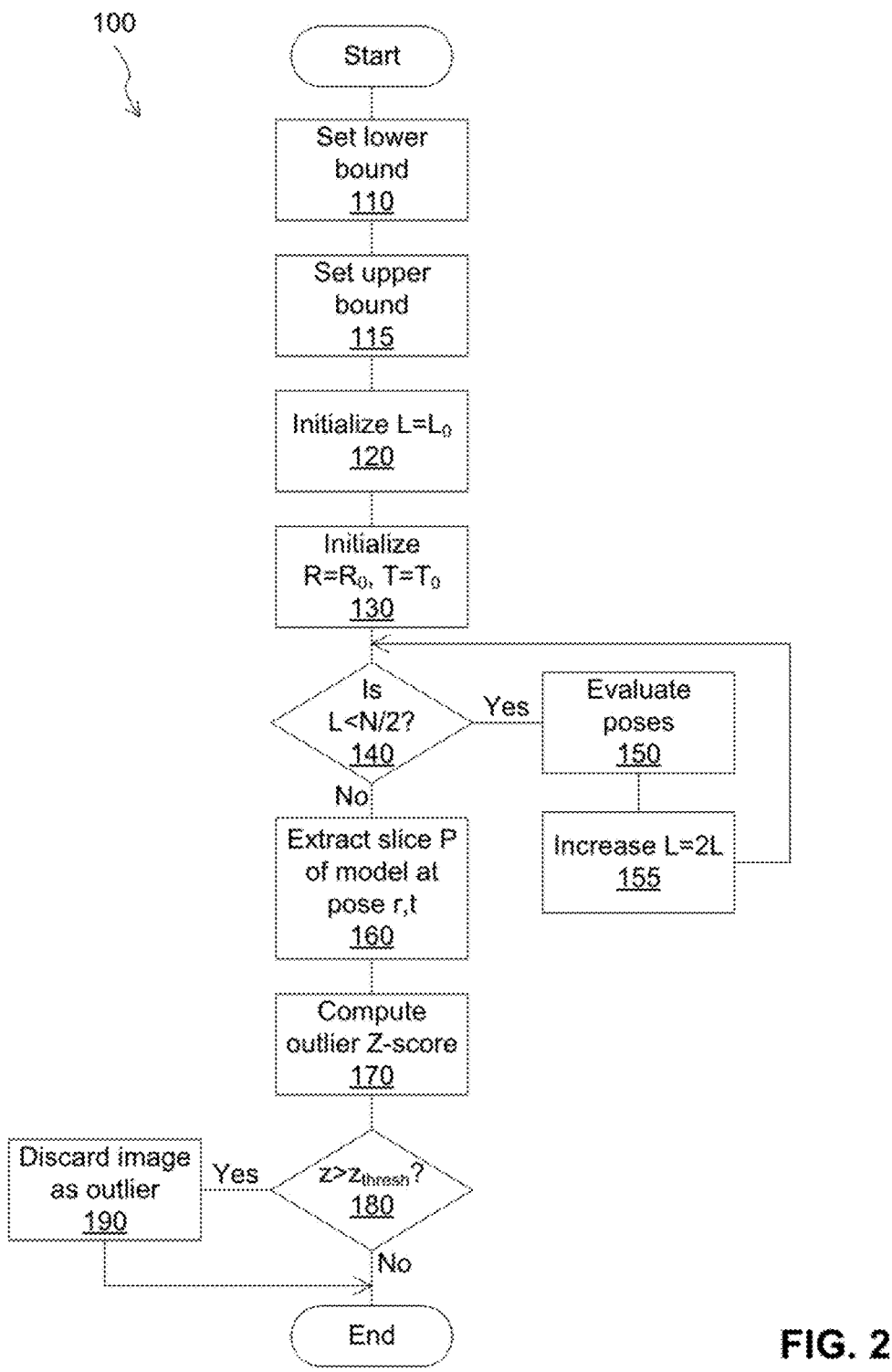
FIG. 2 is a flow chart of the general method for image alignment used by the system of FIG. 1.

A method 100 for image alignment provided herein used by the system 20 in a first implementation, being aligning a 2D image from a Cryo-EM imaging system to a 3D protein structure, will now be described with reference to FIG. 2.

The general problem solved is computing and minimizing of the negative log probability of an image X (2D) given a model M (3D). This is a function of the latent variables describing the pose r and shift t. The likelihood is:

$$p(X|M,r,t) = \frac{1}{z}\exp\left(\Sigma_l \frac{-1}{2\sigma_l^2}|C_l Y_l(r) - S_l(t)X_l|^2\right),$$

where $Y_l(r) = \phi_l(r)M$

Here, both image X and model M are represented in Fourier space. Y(r) denotes the projection of model M along the pose given by r. Poses can be parameterized in any suitable fashion but the axis-angle formulation is applied in the current embodiment. The subscript l denotes a two-component index of a particular Fourier coefficient, also known as a wavevector. For instance l=(0,0) would be the DC component, l=(1,2) would be the Fourier component for wave with 1 cycle in the x-dimension and 2 cycles in the y-dimension. The sum over l is shorthand for summing over all wavevectors in 2D. C denotes the Contrast Transfer Function (CTF) of the microscope (or other image capturing apparatus), and $\phi_l(r)$ is a linear projection operator which in Fourier space is the slice operator with pose r, for wavevector l. S denotes the 2D phase shift corresponding to a shift of t (2D) pixels. Z can be ignored because it does not depend on r, t. The noise model $\sigma_l$ represents the level of Gaussian noise expected in the images, with a possibly different variance for each Fourier coefficient (which allows for white or colored noise models). For clarity in the following, $\sigma_l$ is set to $\sigma_l = \sigma = 1$ but the general case would be apparent to a person of skill in the art. Next, the negative log is taken to arrive at our objective function which ends up being the squared error:

$$E(r,t) = \Sigma_l \frac{1}{2}|C_l Y_l(r) - S_l(t)X_l|^2$$

The goal is to minimize E(r,t) which depends on the image X and model M.

Current approaches to Cryo-EM alignment use exhaustive scan to search over poses and shifts. In exhaustive scan, a discrete set of poses r∈R and shifts t∈T are used and the minimum error pose on this discrete grid is found by directly evaluating E(r,t) at each pose and shift and selecting the best one. In using exhaustive scan, an assumption is made that the sampling used in R and T is fine enough to capture the variations in E(r,t), so that the best looking pose within the discrete grid will actually be close to the minimum of E(r,t).

Unlike local searches, which can also be used to provide a modest speedup, the BnB technique described here is guaranteed to find the best pose in the sets R, T without requiring an exhaustive scan.

The method 100 commences with the setting of a lower bound (110). The core difficulty in employing a BnB approach is to derive bounds that are cheap to evaluate but informative about the objective function E(r,t). This usually requires insight into the characteristics of E.

The setting of the lower bound takes as an assumption that if a 2D image aligns poorly to a 3D structure at low resolution, it will probably not align well at high resolution. This means that if the likelihood of an image is evaluated using only its low resolution Fourier coefficients, this is likely to provide knowledge about which regions of pose and shift space are worth pursuing at high resolution.

The negative log-likelihood is a sum-of-squared-errors. This means that each Fourier coefficient is equivalent, and each contributes independently with equal weight to the total squared error E. The contribution of each Fourier coefficient is related to its power. If a Fourier coefficient in the model with wavevector l has no power, that coefficient will only contribute a term equal to $\frac{1}{2}|X_l|^2$ to E, and that term does not depend on the pose (r,t) and thus does not need to be considered during search. The bound described herein shows and exploits the fact that a Fourier coefficient in the model that has non-zero but small power also gives a small and limited possible pose-dependent contribution to E.

Therefore, if particular Fourier coefficients of the model at higher resolutions have limited power, there is a limit to how much they can impact the squared error E. If the low frequency coefficients already have a certain amount of error at a particular pose and shift, the high frequency coefficients cannot make this much better or worse. This sets a basis for constructing a bound on E that uses inexpensive evaluations of the squared error at low resolutions to bound true values of E, enabling the elimination of search regions after only evaluating them inexpensively at low resolution.

Figure 3A:
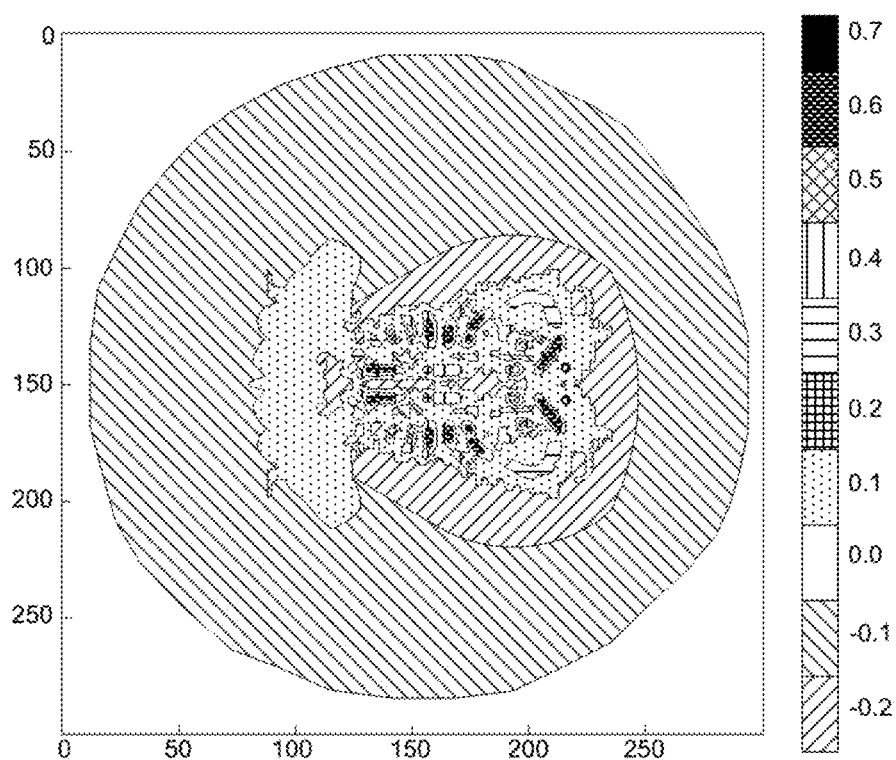
FIGS. 3A to 3C show three slices from the x, y, and z directions of a typical model of a protein in Cryo-EM (TRPA1)
Figure 3B:
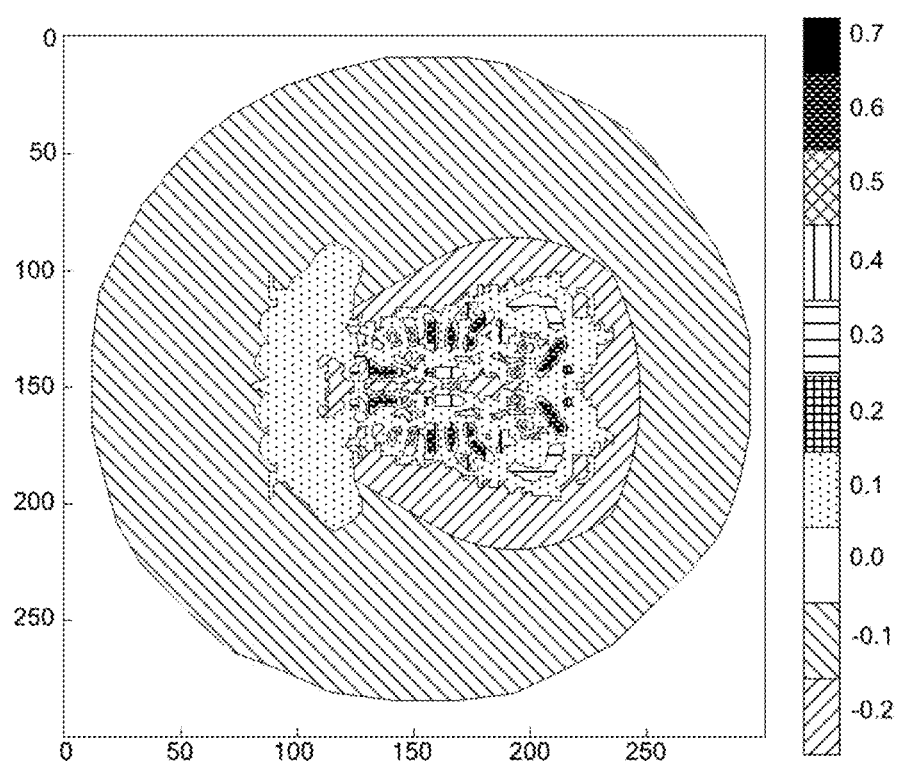
Figure 3C:
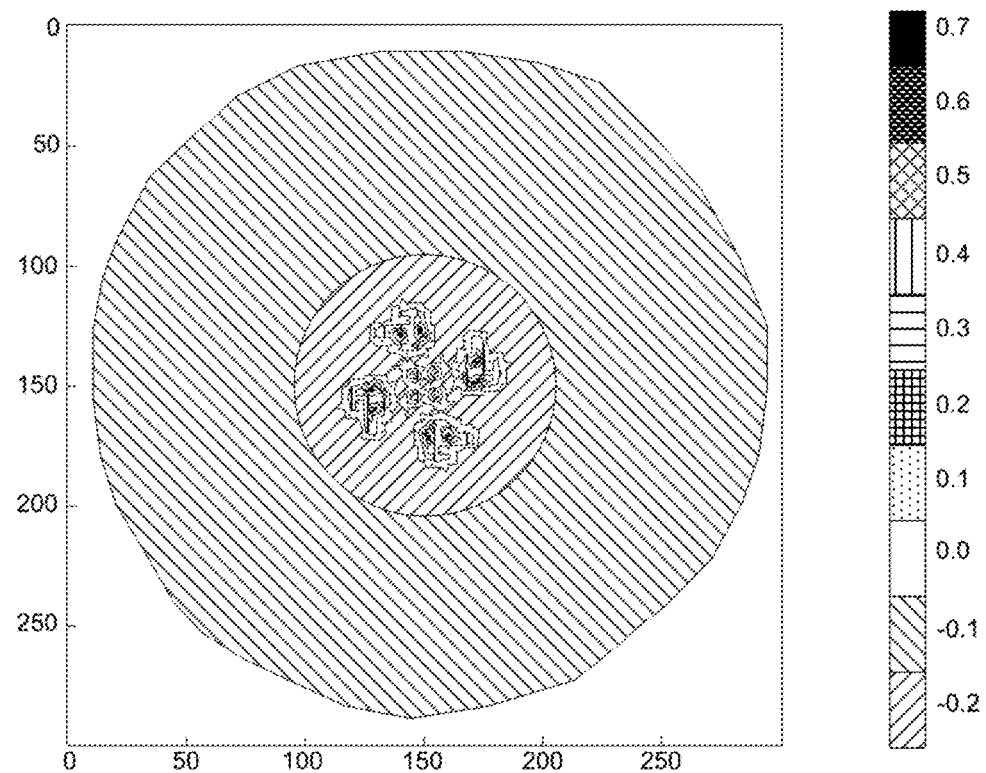
Figure 4:
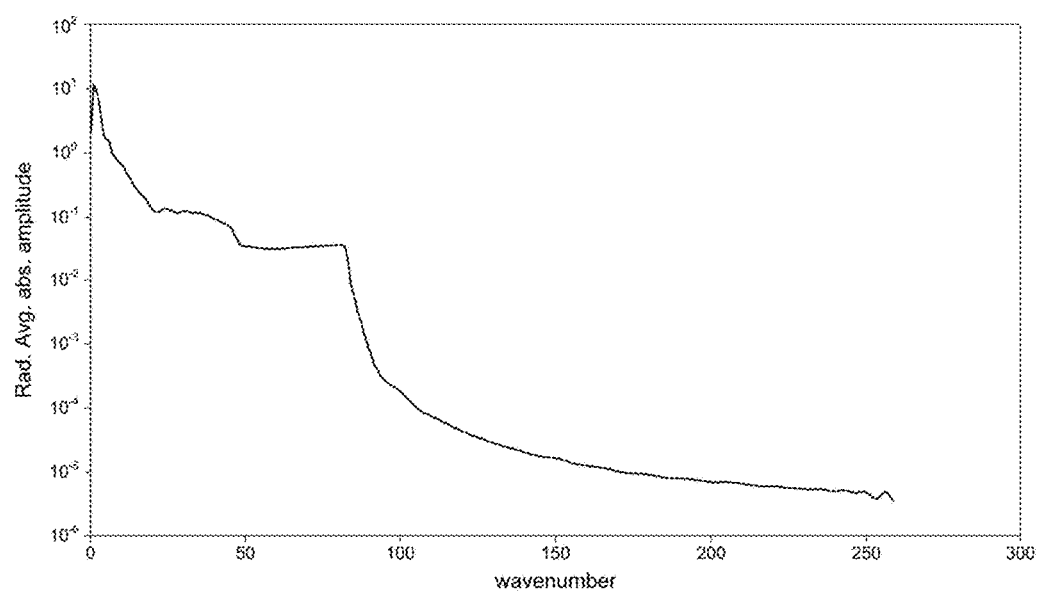
FIG. 4 shows a falloff of model power as a function of frequency.

FIGS. 3A to 3C show three slices from the x, y, and z directions of a typical model of a protein in Cryo-EM (TRPA1). FIG. 4 shows the falloff of model power as a function of frequency and shows that low frequencies have much more power than high frequencies.

It is desired to derive a lower bound that is always less than E. To start, E is split into two parts:

$$E(r,t) = \Sigma_{\|l\| \leq L} \frac{1}{2}|C_l Y_l(r) - S_l(t)X_l|^2 + \Sigma_{\|l\| > L} \frac{1}{2}|C_l Y_l(r) - S_l(t)X_l|^2$$

$$E(r,t) = U(r,t) + V(r,t) \quad (2)$$

Thus, U is the squared error of Fourier coefficients at or below some radius in Fourier space L, and V is the squared error of coefficients above that radius.

In order to bound E, U is directly computed, which is cheap, but V is bounded from below. To do this, V is split into parts.

$$V(r,t) = \Sigma_{\|l\| > L} \frac{1}{2}|C_l Y_l(r) - S_l(t)X_l|^2 \quad (3)$$

$$= \Sigma_{\|l\| > L} \frac{1}{2}|X_l|^2 + \Sigma_{\|l\| > L} \frac{1}{2}C_l^2|Y_l(r)|^2 - \Sigma_{\|l\| > L} \Re(C_l Y_l(r)^* S_l(t)X_l) \quad (4)$$

$$= V_1 + V_2 - V_3 \quad (5)$$

Here, the fact that $|S_l(t)|=1$ is used, and also assumed that the CTF is real-valued. The first term, $V_1$, is the power of the image at high frequencies, and does not depend on r,t. The second term is the power of a slice from pose r of the model at high frequencies. This does not depend on t. The third term is the correlation between the shifted image X and the slice of the model.

First $V_3$ is examined; an upper bound on $V_3$ contributes to a lower bound on V. The Cryo-EM image formation model is employed to start. This model says that the observed image X is a sum of a CTF-corrupted true signal plus independent, identically distributed noise. This means $X_l$ can be written as $X_l = C_l \tilde{X}_l + \eta_l$ where all $\eta_l$'s are independent, identically distributed complex normal random variables with $$\eta_l \sim C\mathcal{N}\left(0, \frac{\sigma_l^2}{2}\right)$$

and it is assumed that $\sigma_l=1$.

This results in $$V_3 = \Sigma_{\|l\|>L} C_l^2 \Re (Y_l(r)^* S_l(t) \tilde{X}_l) + \Sigma_{\|l\|>L} \Re (C_l Y_l(r)^* S_l(t) \eta_l) \quad (6)$$

$$= \Sigma_{\|l\|>L} C_l^2 \Re (Y_l(r)^* S_l(t) \tilde{X}_l) + H \quad (7)$$

$$\leq \Sigma_{\|l\|>L} C_l^2 |Y_l(r)||X_l| + H \quad (8)$$

Here, H is the random variable corresponding to the correlation between the model slice Y(r) and the random noise $\eta$. H indicates how much to reasonably expect the noise to affect E. H can be written as:

$$H = \Sigma_{\|l\|>L} \Re (C_l Y_l(r)^* S_l(t) \eta_l) \quad (9)$$

$$= \Sigma_{\|l\|>L} C_l \Re (Y_l(r)^* \eta_l) \quad (10)$$

$$= \Sigma_{\|l\|>L} C_l \Re \left( Y_l(r) * C\mathcal{N}\left(0, \frac{\sigma^2}{2}\right) \right) \quad (11)$$

$$= \Sigma_{\|l\|>L} C_l \Re \left( C\mathcal{N}\left(0, \frac{\sigma^2}{2} |Y_l(r)|^2\right) \right) \quad (12)$$

$$= \Sigma_{\|l\|>L} \mathcal{N}\left(0, \frac{\sigma^2}{2} C_l^2 |Y_l(r)|^2\right) \quad (13)$$

$$= \mathcal{N}\left(0, \Sigma_{\|l\|>L} \frac{\sigma^2}{2} C_l^2 |Y_l(r)|^2\right) \quad (14)$$

In the first line above, the noise variables $\eta_l$ are uniform over phase, and so are invariant to phase shifting by $S_l(t)$. The final line means that H, the contribution to V from noise in the image, is normally distributed with the variance as given above. The standard deviation of H can be written as $$\sigma_H = \sqrt{\Sigma_{\|l\|>L} \frac{\sigma_l^2}{2} C_l^2 |Y_l(r)|^2}$$

Returning to $V_2$ and $V_3$:

$$V_2 - V_3 = \Sigma_{\|l\|>L} \tfrac{1}{2} C_l^2 |Y_l(r)|^2 - \Sigma_{\|l\|>L} \Re (C_l Y_l(r)^* S_l(t) X_l) \quad (15)$$

$$V_2 - V_3 \geq \Sigma_{\|l\|>L} \tfrac{1}{2} C_l^2 |Y_l(r)|^2 - \Sigma_{\|l\|>L} C_l^2 |Y_l(r)||\tilde{X}_l| - H \quad (16)$$

$$= \Sigma_{\|l\|>L} \tfrac{1}{2} (C_l^2 |Y_l(r)|^2 - 2 C_l^2 |Y_l(r)||X_l|) - H \quad (17)$$

$$= \tfrac{1}{2} (Y(r)^T D Y(r) - 2 Y(r)^T D \hat{X}) - H \quad (18)$$

Equation 18 is written in vector form. Y(r) is a vector where each element is the absolute value of a Fourier coefficient $|Y_l(r)|$. Similarly X is a vector of $|\tilde{X}_l|$. D is a diagonal matrix of the CTF squared. Equation 18 is a quadratic form in Y(r). Turning again to the image formation model it is assumed that in the image, the true signal $\tilde{X}$ is actually a slice of the model in Fourier space. That means that $\tilde{X}$ is a slice of M from the true pose pose $r^*$; $\tilde{X}_l = Y_l(r^*)$. Since Equation 18 is a quadratic form in Y(r) with a positive semi-definite Hessian D, it can be said that the minimum of this expression with respect to Y(r) occurs when $Y(r) = \tilde{X}$. This is attained when $r = r^*$ is chosen, meaning that the value of the expression at its minimum is $-\tfrac{1}{2} \tilde{X}^T D \tilde{X} - H$. Finally, since the true signal $\tilde{X}$ is unknown, this value is unknown. However, since it is known that $\tilde{X}_l = Y_l(r^*)$, it can be said that at minimum, it will be $$-\frac{1}{2} \tilde{X}^T D \tilde{X} \geq \min_r -\frac{1}{2} Y(r)^T D Y(r)$$

attained at $\hat{r}$ with $\hat{Y} = Y(\hat{r})$. This is a value that can be easily computed for the given model M, since it is independent of the image X and also doesn't depend on poses or shifts r, t. It is the CTF-corrupted power at high frequencies of the slice of M that has the most power.

Thus, it is finally arrived at $$V_2 - V_3 \geq -\Sigma_{\|l\|>L} \tfrac{1}{2} C_l^2 |\hat{Y}_l|^2 - H$$

From the above, it follows that:

$$E(r,t) \geq U(r,t) + V_1 - \Sigma_{\|l\|>L} \tfrac{1}{2} C_l^2 |\hat{Y}_l|^2 - H$$

Due to the presence of H, this expression provides a probabilistic bound on E, indicating that the probability of E is greater than the value of the expression. In an example, a probability, 0.999936, which corresponds to four standard deviations of H, is selected to arrive finally at the lower bound on E(r,t):

$$E(r,t) \geq U(r,t) + V_1 - \Sigma_{\|l\|>L} \tfrac{1}{2} C_l^2 |\hat{Y}_l|^2 - 4\sigma_H \quad (19)$$

$$= U(r,t) + V_1 - \Sigma_{\|l\|>L} C_l^2 \frac{1}{2} |\hat{Y}_l|^2 - 4\sqrt{\Sigma_{\|l\|>L} \frac{\sigma^2}{2} C_l^2 |Y_l(r)|^2} \quad (20)$$

$$\geq U(r,t) + V_1 - \Sigma_{\|l\|>L} \frac{1}{2} C_l^2 |\hat{Y}_l|^2 - 4\sqrt{\Sigma_{\|l\|>L} \frac{1}{2} C_l^2 |\hat{Y}_l|^2} \quad (21)$$

$$= B_L(r,t) \quad (22)$$

In the last line, the maximum power slice $\hat{Y}$ is again used, and that σ=1.

At this point, an expression is arrived at which, with very high probability, bounds E(r,t) from below. This expression is cheap to compute for an particular r, t (since only U depends on these), and the remainder only needs to be computed once for all r, t, and also only once for all images that share the same CTF; i.e., that come from the same micrograph. To compute the bound, it is only needed to find the slice of the model which has the most power ($\hat{Y}$). Then the expression is used to compute the values of U and the power of the image $V_1$.

The bound above is actually a family of bounds, one for each radius L. As L is increased, the bound becomes more expensive but tighter, and finally when L reaches the Nyquist rate then the bound becomes exact, but is as expensive as directly computing E(r,t).

Returning to FIG. 2, upon establishing a lower bound, an upper bound is established (115).

As an upper bound on E(r,t), a single direct evaluation of E at a specific pose and shift can be used. During optimization, a candidate best pose and shift r*,t* are maintained, and are used to compute E*=E(r*,t*), the upper bound on the minimum of E. It can be said that the minimum of E(r,t) can not be greater than E*, because that would be a contradiction —every E(r,t) for all r, t must be greater or equal to the value at the minimum.

Figures 5, 5A, 5B, 5C, 5D:
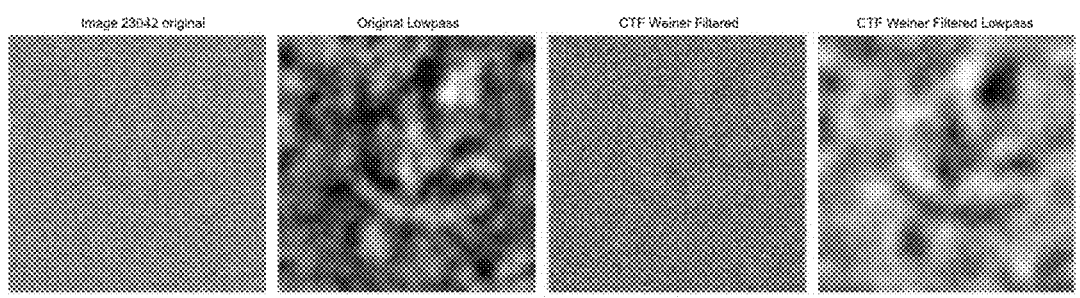
FIG. 5A shows an image taken with a Cryo-EM of a protein.
FIGS. 5B to 5D show the image of 5A after application of various filters.

FIG. 5A shows an image of a protein taken with an electron microscope. FIGS. 5B to 5D show the image of 5A after application of various filters.

Figure 6:
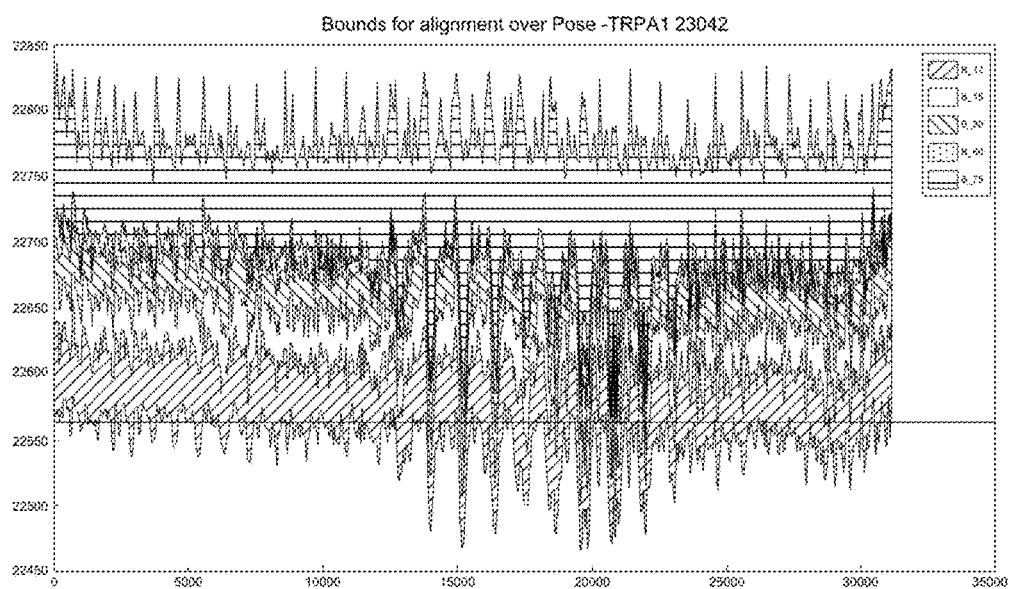
FIG. 6 shows the values of a bound over poses r, taking the minimum over all shifts to arrive at the values for each r.
Figure 7:
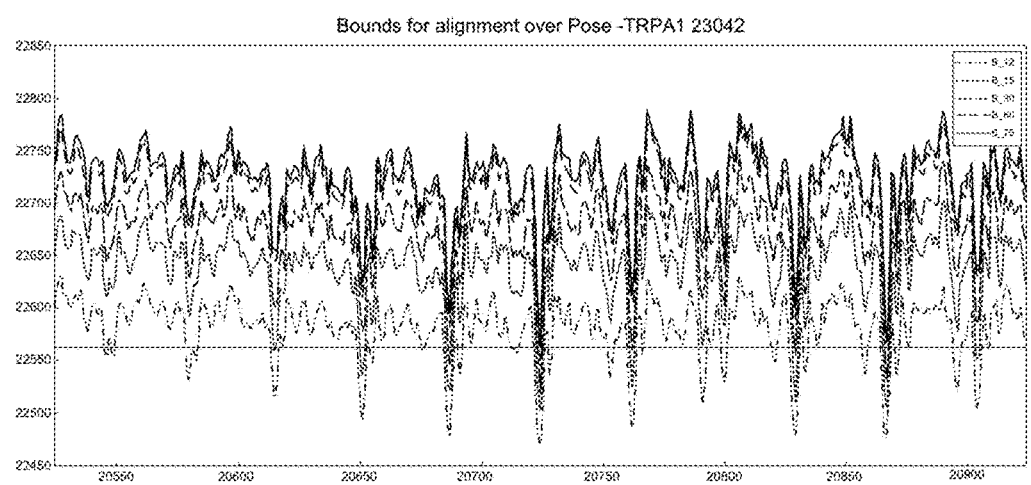
FIG. 7 shows a zoomed in section of the graph of FIG. 6 near the true best pose.
Figure 8:
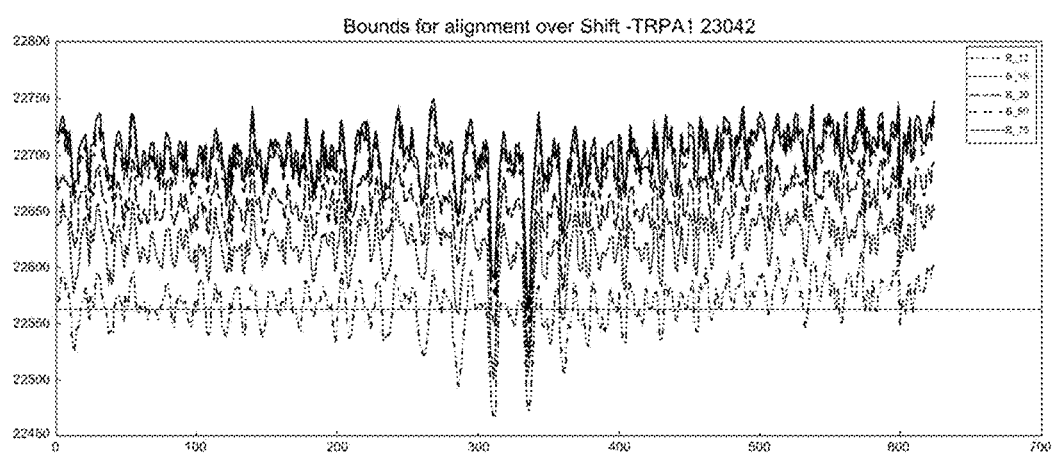
FIG. 8 shows the same bounds as FIGS. 6 and 7, but over shifts rather than poses.

FIGS. 6 to 8 show values of the lower bound $B_L$(r,t) at various levels L for the image of FIG. 5A showing lower and upper bound being useful at different radii. In each plot, the black horizontal line is an upper bound E*, while the other lines are the lower bounds. After evaluating a single bound, say $B_{12}$, only the regions below the horizontal black line need to be re-evaluated at a higher level, say $B_{30}$. The true minimum of E must be between the upper and lower bounds. FIG. 6 shows the values of a bound over poses r, taking the minimum over all shifts to arrive at the values for each r. Each position on the x-axis of the plot corresponds to the index of a unique pose r on a grid covering all possible poses. FIG. 7 shows a zoomed in section of the graph of FIG. 6 near the true best pose. Note that the upper bound intersects the lower bounds, meaning that evaluating a lower bound (rather than the full objective E(r,t)) allows one to discard vast regions of the pose space. Also note that the family of bounds $B_L$ becomes tighter (higher) with increasing L, until finally the upper and lower bounds meet at the true minimum of the objective. FIG. 8 shows the same bounds, but over shifts t rather than poses. Each position on the x-axis corresponds to a unique position on a grid covering a range of possible shifts.

The lower bound derived above, $B_L$(r,t), can be used to develop a method to search over poses and shifts faster than exhaustive search without loss of alignment accuracy. With the theoretical support of the bound in place, very similar but more effective approximate bounds and techniques are described.

Referring again to FIG. 2, from the starting point of exhaustive search, the following BnB optimization using the bound $B_L$ is introduced. Here $R_0$ and $T_0$ are the discrete grids that would have been used for exhaustive search. L is initialized as L=$L_0$ (120). R and T are initialized as R=$R_0$, T=$T_0$ (130). While it is determined at 140 that a selected accuracy of image alignment has been obtained, in this case being that L is less than the Nyquist rate, poses are evaluated (150), after which L is doubled (155). In further cases, the selected accuracy of image alignment has been obtained when a selected number of iterations have been performed.

Figure 9:
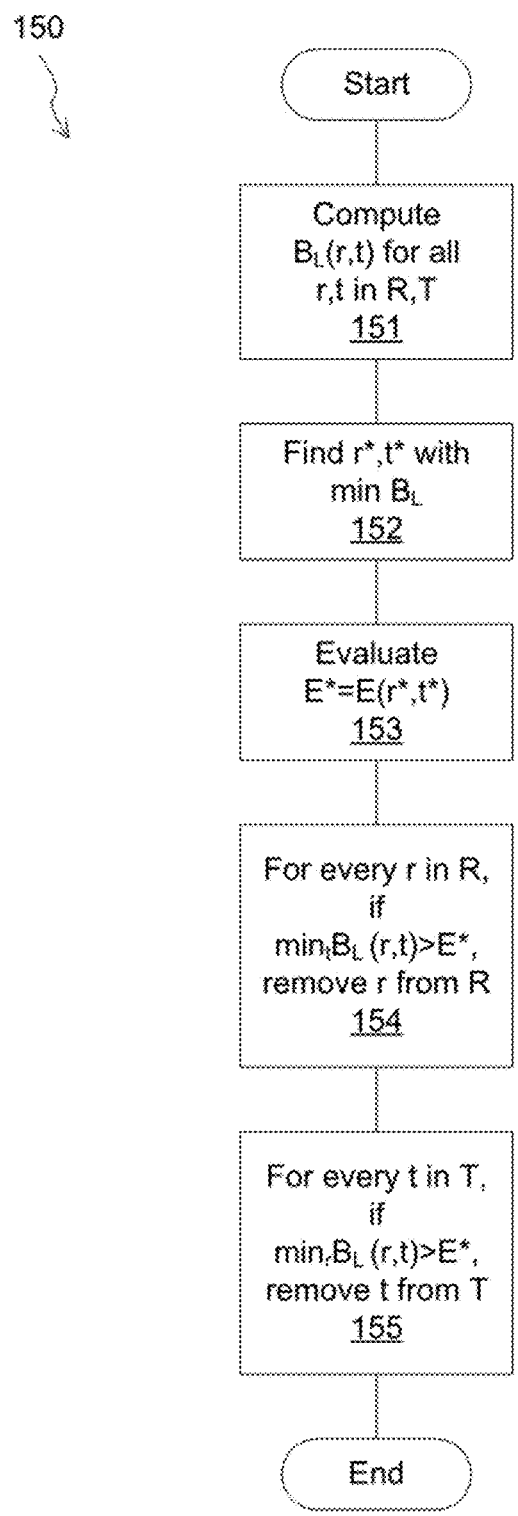
FIG. 9 shows the process of evaluating poses of FIG. 2 in accordance with a first implementation.

FIG. 9 shows the process of evaluating poses at 150. $B_L$(r,t) is computed for all r, t in R, T (151). The r*,t* with minimum $B_L$ are located (152). E*=E(r*,t*) is evaluated (153). For every r in R, if $\min_t B_L$(r,t) is greater than E*, r is removed from R (154). For every t in T, if $\min_r B_L$(r,t) is greater than E*, t is removed from T (155).

Returning again to FIG. 2, once L≥N/2, r*,t* are returned, which represent the pose and shift of the optimal alignment of the image to the structure.

As this technique progresses, poses and shifts are identified that cannot be the minimum E because the lower bound at that pose is greater than the current best value of E. As these points are identified, they are removed from the set of candidate poses and shifts. Upon termination, only the pose and shift with minimum E will remain.

Note that this method begins by evaluating $B_{L_0}$(r,t) for all of R, T, as opposed to exhaustive scan, which would have evaluated E(r,t) for all R, T. The cost of computing E(r,t) is proportional to $(N/2)^2$ and the cost of computing $B_L$(r,t) is proportional to $L^2$. This means that, at best, the speedup that can be achieved with this technique is $$\left(\frac{N/2}{L_0}\right)^2.$$

In some scenarios this is about 100, but speedups on the order of 20-30 can be achieved in other scenarios.

The bound described above gives a strong theoretical backing for the assumption, and also allows modest speedups to be achieved.

First Level Approximations

In another implementation, some approximations can be made to yield a method that is similar, but provides much larger speedups. The existence and tightness of bound $B_L$(r,t) indicate that low-resolution alignment provides significant information about high-resolution alignment.

Consider first bound $B_L$. To compute it, the slice Y of model M which has the largest CTF-corrupted power can be found. One drawback of this computation is that it needs to be redone for each set of images that has a different CTF. The CTF, at frequencies above L, is like a sine function with a varying frequency. The RMS power of the CTF is thus close to $1/\sqrt{2}$. An approximation can be made and it can be assumed that $$\Sigma_{\|l\|>L}\frac{1}{2}C_l^2|\hat{Y}_l|^2 \approx \frac{1}{2}\Sigma_{\|l\|>L}\left(\frac{1}{\sqrt{2}}\right)^2|\hat{Y}_l|^2 = \Sigma_{\|l\|>L}\frac{1}{4}|\hat{Y}_l|^2$$

This expression no longer depends on the CTF, so the approximate bound can be entirely independent of the image, and only needs to be computed once, given the model. Note that this approximation of the CTF does not actually make the bound tighter, rather it removes the dependence on the image.

Again consider the above expression. A search is performed over slices Y to find the one with the maximum power. The maximum power slice, $\hat{Y}$, gives a strict limit on how much power there could be at high frequencies that might contribute to E. However, it is very unlikely that for any given image, the true pose will be the same as the pose of $\hat{Y}$, since most images do not come from the maximum power slice. Thus, the slice $Y^\dagger$ that has the median power of all slices can be used as an approximation instead of the maximum (or any other rank statistic).

All together, the above approximations lead to an approximate lower bound for E(r,t) as $$A_L(r, t) = U(r, t) + V_1 - \Sigma_{\|l\| > L} \frac{1}{4} |Y_l^\dagger|^2 - 4\sqrt{\Sigma_{\|l\| > L} \frac{1}{4} |Y_l^\dagger|^2}$$

So far, the approximations allow for the construction of an approximate bound that is inexpensive, but this is still limited in the same way as the application of the true bound in speeding up exhaustive scan (previous implementation). To overcome this limitation, the following assumption is applied: when the bound at low resolutions (low L) is evaluated, the sampling need not be nearly as fine in pose and shift space as needed when searching at high resolution. At low L, coarse sampling along with the bounds themselves can allow the identification of regions that need to be searched further at high L and finer sampling.

One way to understand why a coarse (at low resolution) to fine (at high resolution) sampling approach is reasonable is to consider the angular spacing of Fourier coefficients in each Fourier shell of a 3D structure. This spacing is much larger at low resolutions than at high resolutions.

A stronger argument can be made by considering the fact that the 3D structure in real space is compact and has a small extent relative to the full volume. This is true because of the masking that is applied during refinement of a 3D structure for Cryo-EM. Usually, in Fourier analysis, if the Fourier transform F(i,j,k) of a real-space signal f(x,y,z) has no power a distance d away from the origin of Fourier space, it can be said that the real-space f is 'band-limited', has no high-frequency power, and is thus smooth. The Fourier transform, however, is a unitary transform, so this argument can be exactly inverted. It can be said that if a real-signal f has no power a distance d away from the origin of real space, then the Fourier transform F must be smooth. This reasoning indicates that $B_L(r,t)$, which depends on slices of the 3D Fourier transform of a masked structure, is smooth with respect to r, t. The smoothness is strongest when L is small.

A technique can be used to exploit this notion of smoothness. The pose and shift space are first subdivided into cells on a coarse grid $R_0$, $T_0$. On this grid, the (approximate) bound is evaluated at a low value of L. This allows for the identification of cells that may contain the minimum E. All those cells are kept as candidates. Each candidate cell is then subdivided by a factor of 2 in each dimension, increase L, and repeat the process.

Domain subdivision of this type removes the speedup limitation from the previous sections. With domain subdivision, approximate branch and bound alignment can reach several orders of magnitude of speedup relative to exhaustive scan.

Together, the approximate bounds and subdivision scheme allow for the construction of an effective technique for alignment.

Figure 10:
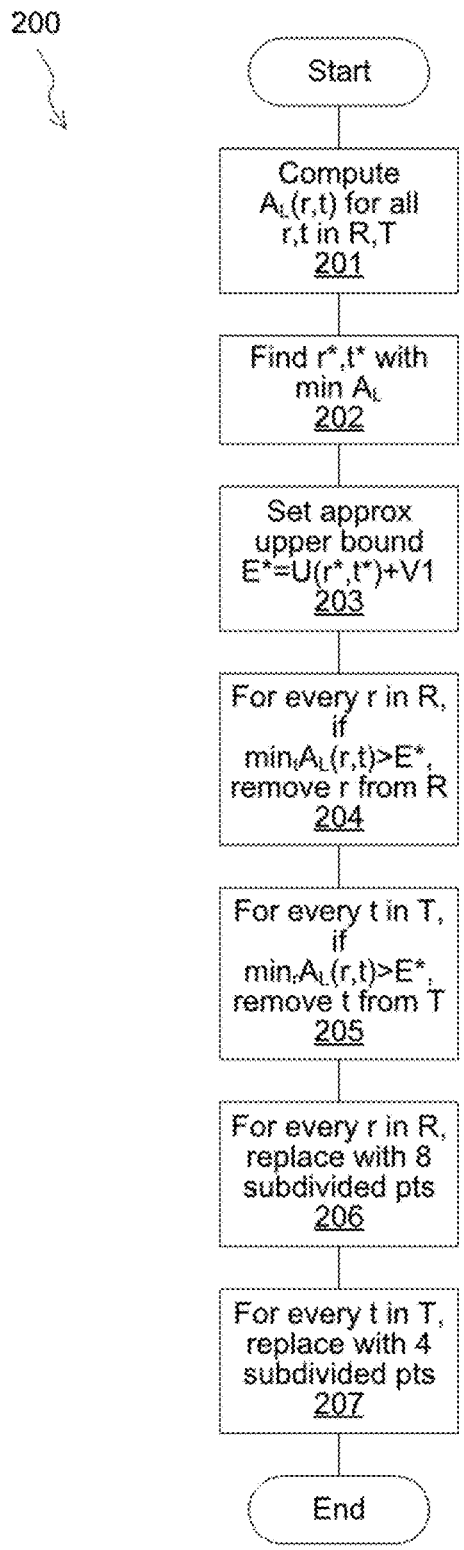
FIG. 10 shows the process of evaluating poses of FIG. 2 in accordance with a second implementation that uses first level approximations.

The process of evaluating poses in this implementation is shown generally at 300 in FIG. 10. $A_L(r,t)$ is computed for all r,t in R,T (approximate lower bound) (201). The r*,t* with minimum $A_L$ are then located (202). E* is set to E*=E(r*,t*) (203). For every r in R, if $\min_t A_L(r,t)$ is greater than E*, r is removed from R (204). For every t in T, if $\min_r A_L(r,t)$ is greater than E*, t is removed from T (205).

Replace every r in R with κ subdivided points (206). Replace every t in T with 4 subdivided points (207).

This process in this second implementation works very well on real data, achieving significant speedups in many cases. There is one tuning parameter, the coarseness of the initial grids $R_0$ and $T_0$, that allows a trade-off between accuracy and speed. On real images, even liberal settings of this parameter do not affect the quality of alignments, but give significant speedups.

Second Level Approximations

In a further implementation, a further simplified approximate version of the BnB optimization is developed that can be implemented very simply. Empirically, this further simplified approximate version produces alignments of high quality on real data, resulting in high resolution 3D structures, while being extremely fast.

In practice, the bound and approximate bound presented in earlier sections reject large regions of the pose space, for most images. On some images, however, the bounds do not reject enough of the pose space at each iteration of the alignment technique, meaning that the method does not provide much speedup on those images.

On further observation, for a typical dataset, it is only a small fraction of images that perform poorly, and that these images are actually outlier images, meaning that they are not images of the structure to which alignments are computed. They may be images that were incorrectly picked from micrographs, or they may be images of broken/damaged particles. The characteristic of these images is that they break the assumptions that make the bound tight (and thus fast). These assumptions are that the observed image is a noisy slice from the model M, and that the image has the correct formation and noise model. In a following section, it is discussed how to directly detect the breaking of these assumptions and thus reject outlier images outright.

To deal with the problem of some pathological images in alignment, the upper bound is replaced with a fixed fraction $f_{keep}$. At each iteration of the alignment technique, only the best $f_{keep}$ of the candidate poses and shifts are kept, discarding the rest. This effectively means that all images will take the same amount of computation to align, and the value of $f_{keep}$ will be another trade-off parameter between speed and accuracy. Using this modification to the alignment technique eliminates the need for even computing the upper or lower bounds.

The fraction of poses and shifts that are discarded on typical images on a typical dataset using the approximate bound are empirically examined, and $f_{keep}$ is set accordingly. The Applicant has determined that, in some cases, a fixed fraction $f_{keep}$ of between 3% and 10% is effective. In a further case, the Applicant has determined that a fixed fraction $f_{keep}$ of approximately 5% is effective.

Figure 11:
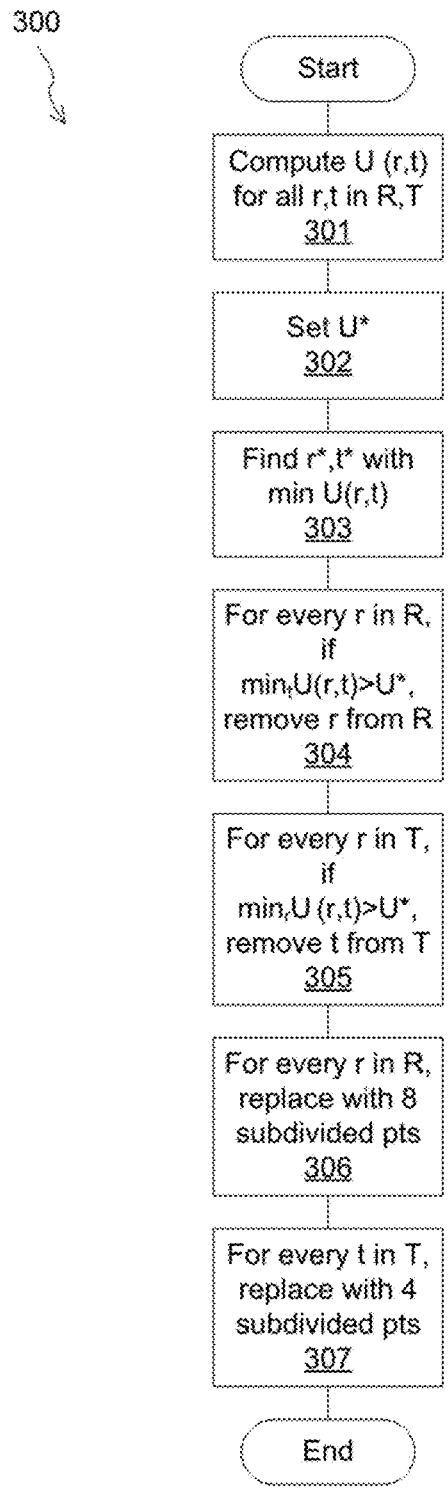
FIG. 11 shows the process of evaluating poses of FIG. 2 in accordance with a third implementation that uses second level approximations.

The process of evaluating poses in this implementation is shown generally at 300 in FIG. 11. U(r,t) is computed for all r,t in R, T (301). U* is set so that $$\frac{|\{(r, t); U(r, t) \le U^*\}|}{|\{(r, t); U(r, t) > U^*\}|} = f_{keep}$$

(302). The r*,t* with minimum U(r,t) is located (303). For every r in R, if $\min_t U(r,t)$ is greater than U*, r is removed from R (304). For every t in T, if $\min_r U(r,t)$ is greater than U*, remove t from T (305). Replace every r in R with 8 subdivided points (306). Replace every t in T with 4 subdivided points (307).

Although this implementation does not guarantee optimal alignment, it is an approximation of the mathematically sound technique and bound proven to be correct earlier. This, along with excellent empirical performance, sets it apart from existing heuristics.

To demonstrate the empirical performance of the alignment technique using second level approximations, 3D structures reconstructed using the technique on two different datasets are shown, together with the computational time it took to recover these structures.

Figure 12A:
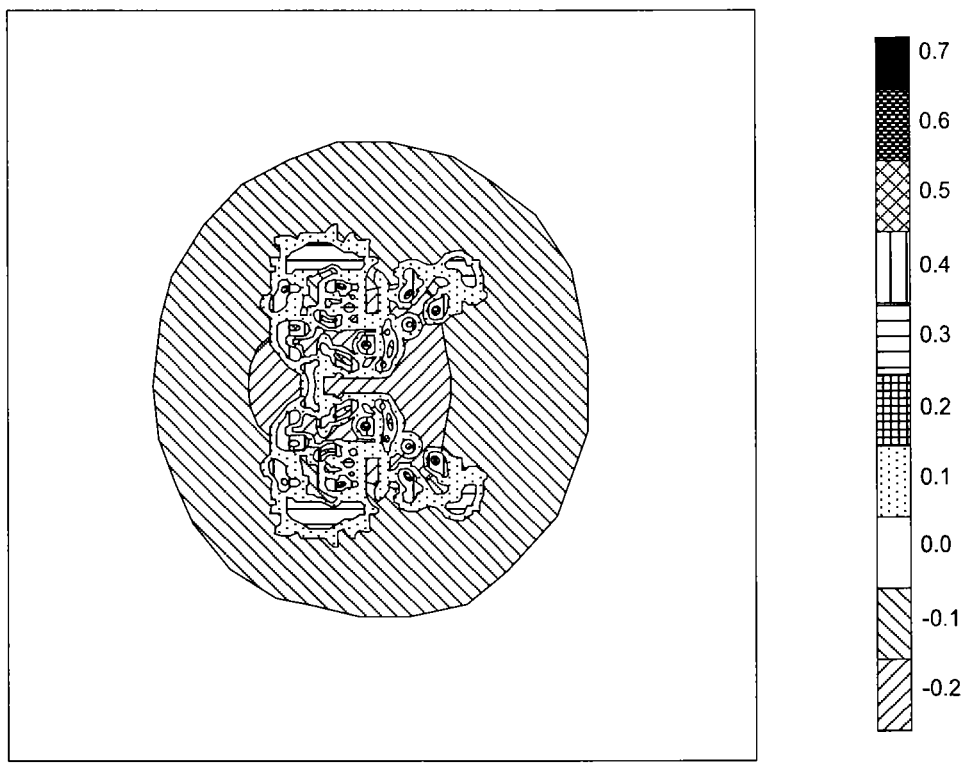
FIGS. 12A to 12C show three slices from the x, y, and z directions of a protein reconstruction result in Cryo-EM (TRPV1)
Figure 12B:
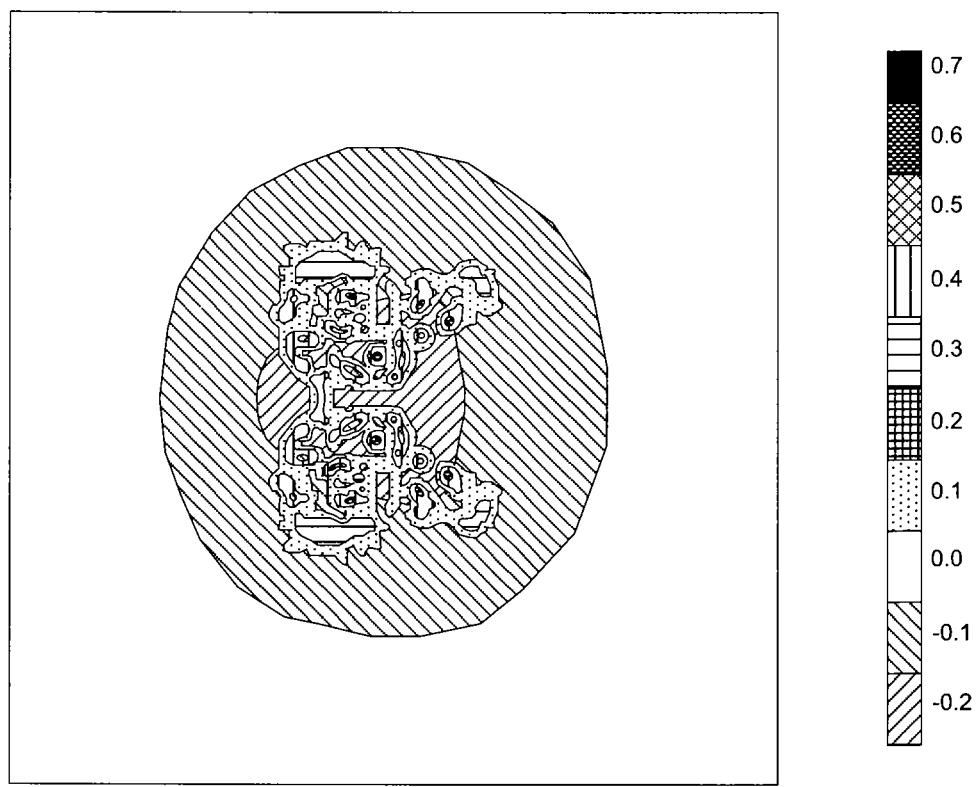
Figure 12C:
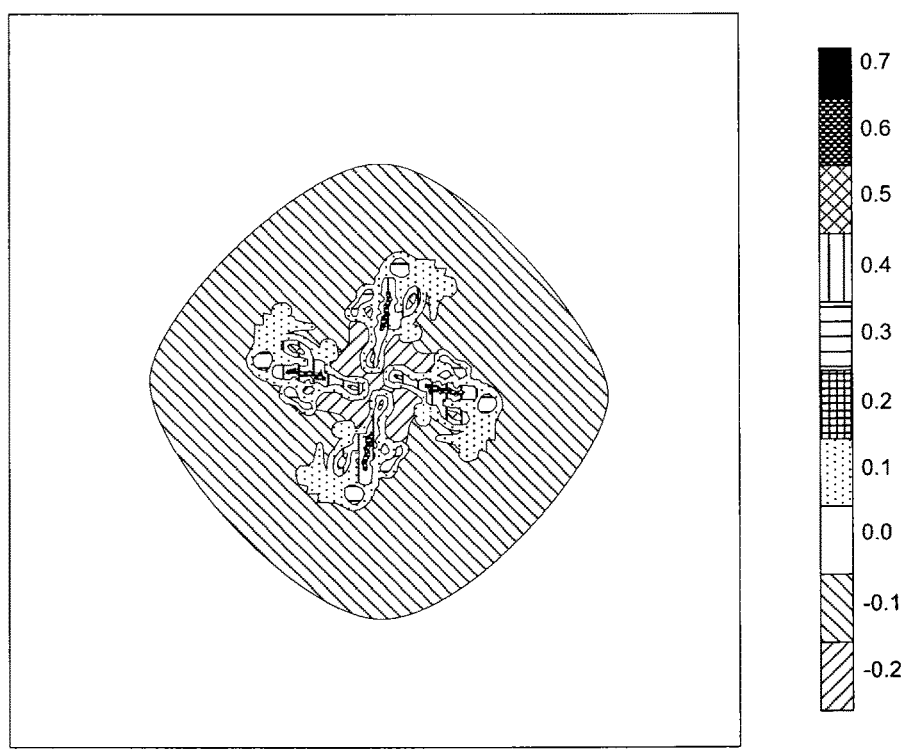
Figure 13:
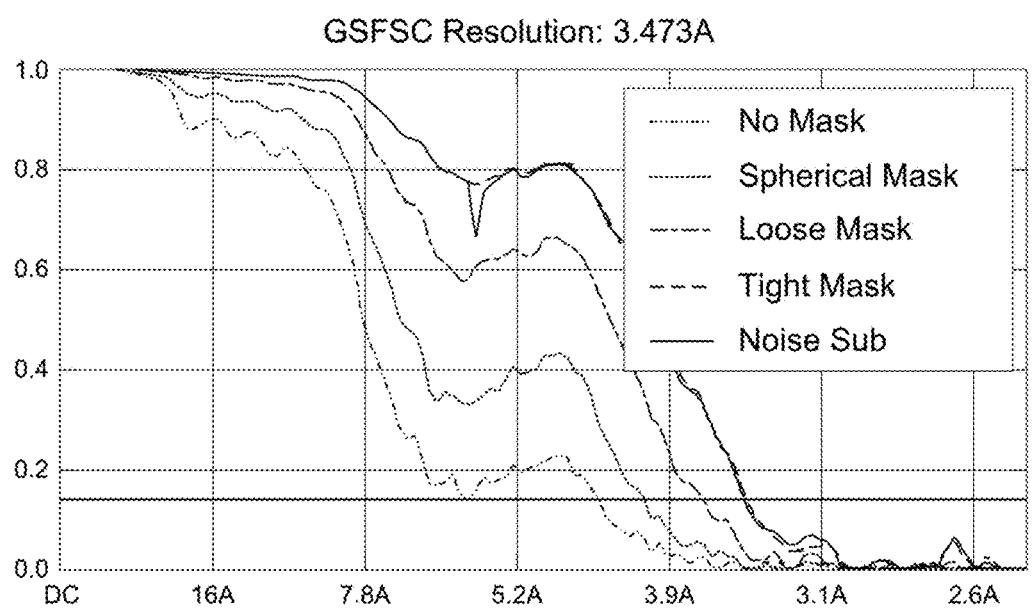
FIG. 13 is an FSC resolution estimate of the protein of FIGS. 12A to 12C.
Figure 14:
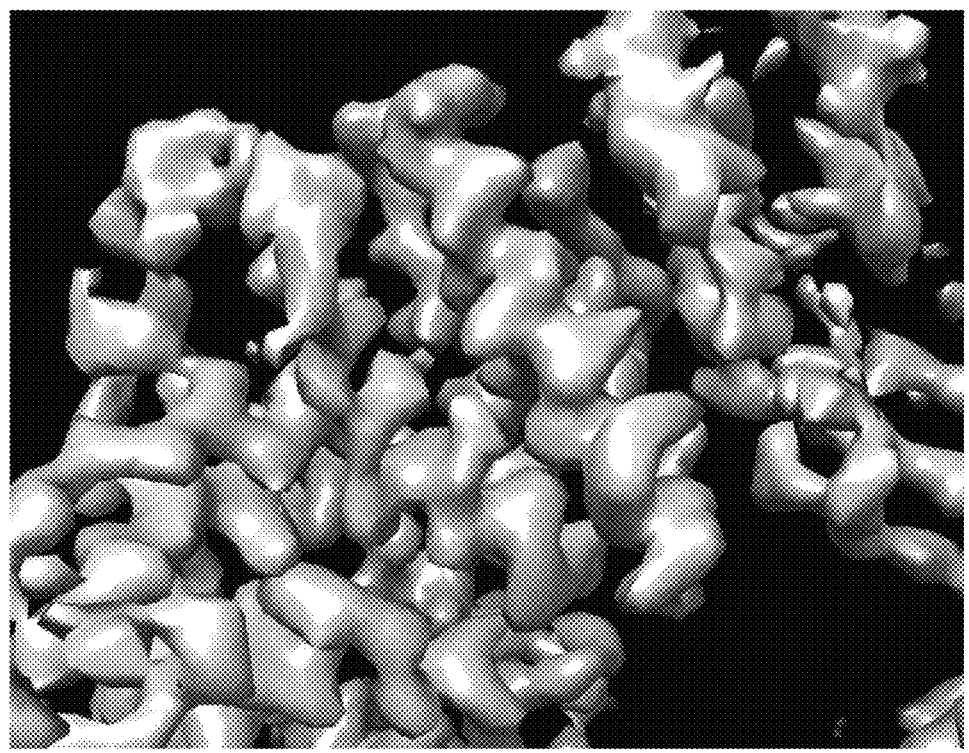
FIG. 14 is a rendered image of the reconstruction of the determined structure(s) of FIGS. 12A to 12C.

FIGS. 12A to 12C show three slices from the x, y, and z directions of a result of the determination of the three-dimensional structure of the TRPV1 protein using the alignment technique presented herein. FIG. 13 is an Fourier Shell Correlation (FSC) resolution estimate of the result in FIGS. 12A to 12C. FIG. 14 is an image that illustrates the quality of the structure reconstructed using the process of the third implementation, with side-chains visible in alpha helices. This structure was computed in less than one hour on a single desktop GPU-workstation.

Figure 15A:
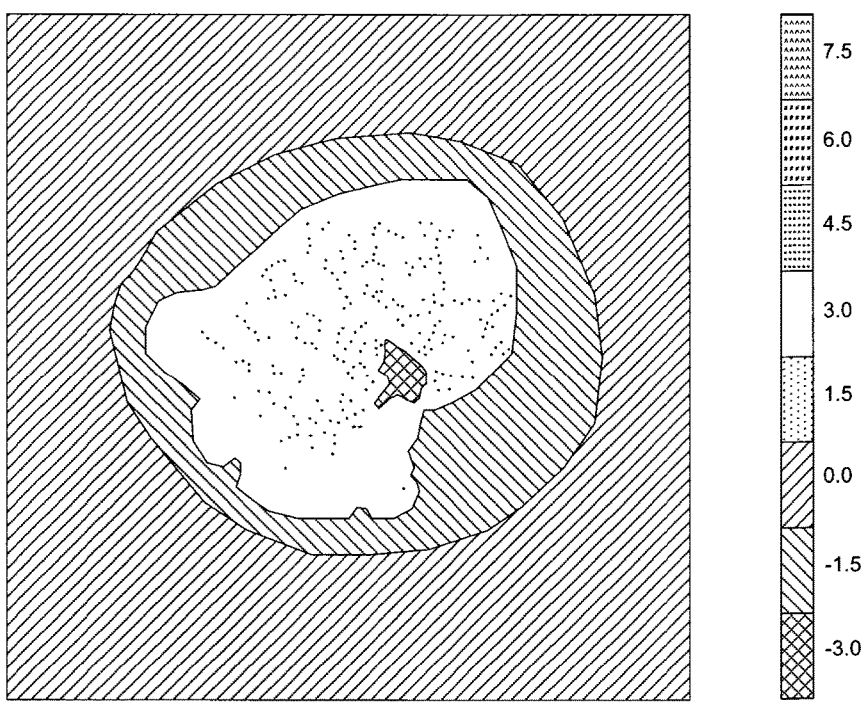
FIGS. 15A to 15C show three slices from the x, y, and z directions of a reconstructed ribosome protein in Cryo-EM.
Figure 15B:
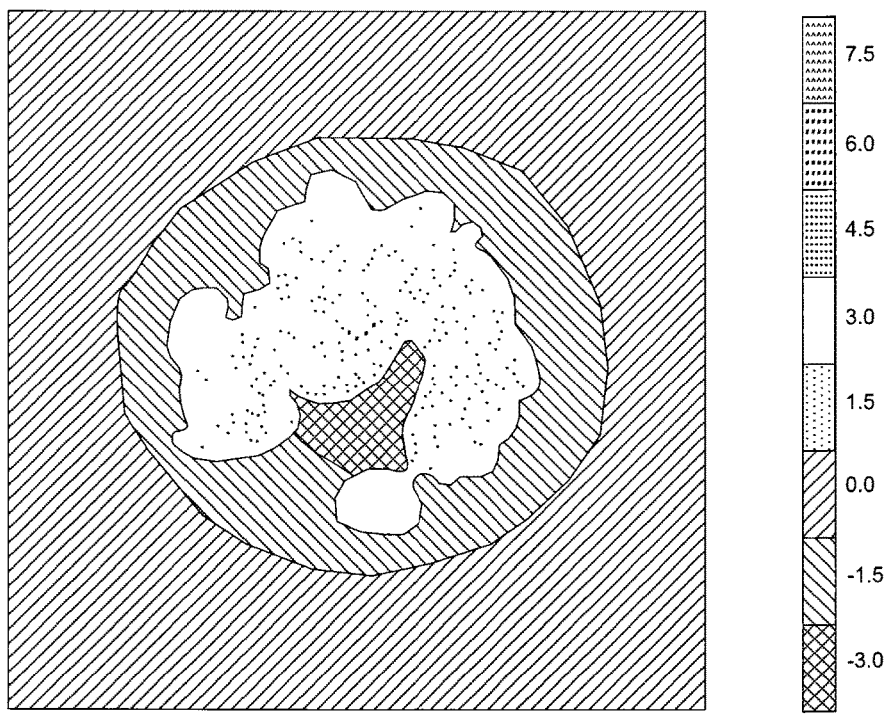
Figure 15C:
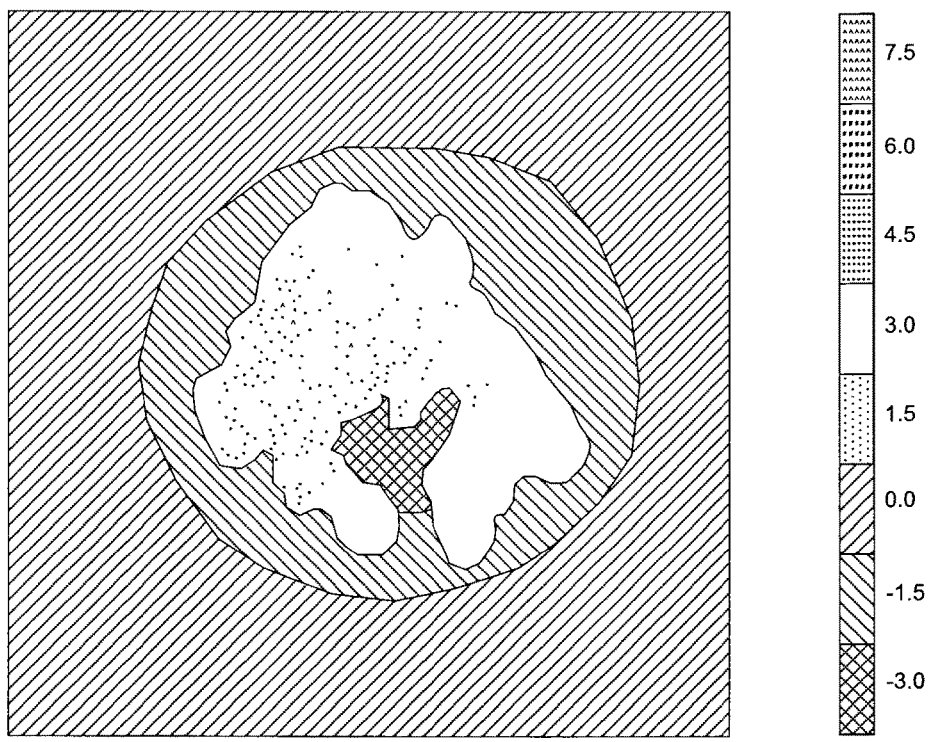
Figure 16:
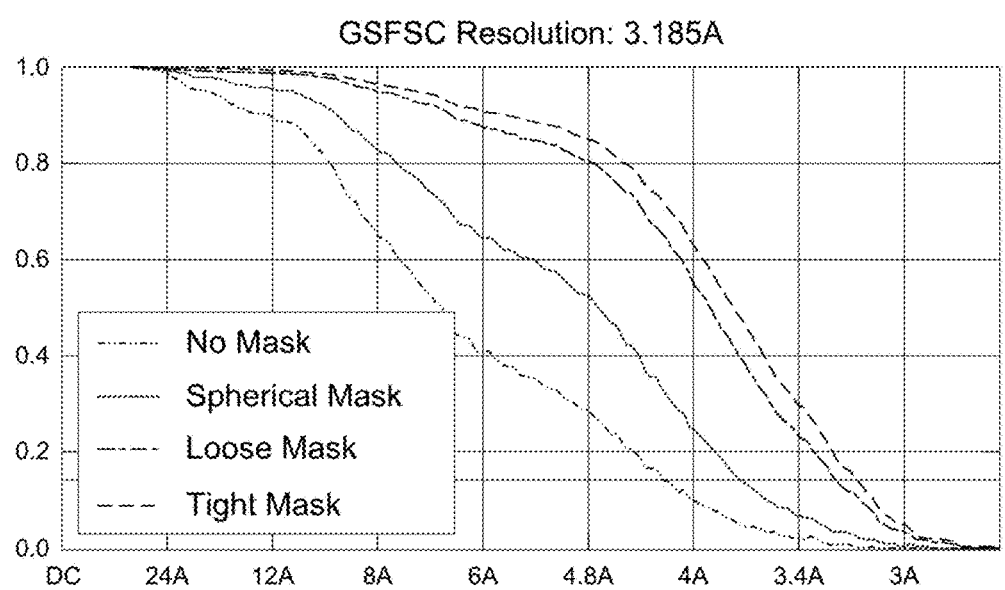
FIG. 16 is an FSC resolution estimate of the ribosome of FIGS. 15A to 15C.

FIGS. 15A to 15C show three slices from the x, y, and z directions of a result of the determination of the three-dimensional structure of the 80S ribosome protein using the alignment technique presented herein. FIG. 16 shows an FSC resolution estimate of the result in FIGS. 15A to 15C. This structure was computed again in less than two hours on a single desktop GPU-workstation.

Representation, Discretization and Subdivision of Pose (r) and Shift (t)

In the present embodiments, poses and shits are represented by numerical vector quantities. The present embodiments apply three-dimensional vectors to encode poses using the axis-angle formulation; however, it is appreciated that poses can be parameterized in any suitable fashion. The present embodiments parameterize shifts by applying two-dimensional vectors with units of pixels of shift in the horizontal and vertical directions; however, it is appreciated that shifts can be parameterized in any suitable fashion.

The space of poses, as vectors in the axis-angle formulation, comprises a sphere of radius $\pi$ centered at the origin. This space can be discretized into a grid of possible poses where each pose is a three-dimensional grid point. The grid can be instantiated with a desired fineness, to cover the sphere of radius $\pi$. Once a grid is instantiated with a grid spacing of d, it can be subdivided into a grid of finer coarseness by splitting the grid in each dimension into grid cells of size d/2. This yields eight new subdivided grid cells for each grid cell in the original grid.

Similarly, the space of shifts of an image can be discretized into a two dimensional grid of desired fineness covering a desired range of image shifts. This two dimensional grid of grid spacing d can be subdivided by splitting each grid cell into four cells of size d/2.

The representations, discretizations and subdivision methods, described herein, can also be applied when the pose space is one-dimensional or when the shift space is three dimensional, as may be the case in other embodiments.

Termination Criteria

In the above-described implementations, the coarseness of the initial pose and shift grids determines the precision that is reached after K iterations of subdivision. In practice, alignment iterations are not terminated when $L \geq N/2$, but rather continue until the precision of alignment reaches a reasonable level. This level can be determined using a common measure of how well the grid is sampling E(r,t), known as the Effective Sample Size:

$$e = \frac{1}{\sum_{r,t} \left( \frac{\exp(-E(r, t))}{\sum_{r,t} \exp(-E(r, t))} \right)^2}$$

This value e represents the number of poses and shifts that have significant probability of being the correct pose. On a coarse grid, there may only be one pose or shift that has significant probability. As the pose and shift grids are subdivided, e increases. Once e reaches a minimum value $e_{min}$ for the majority of images being aligned (i.e. the median e over images), alignment can be terminated. Typical values are $2 \leq e_{min} \leq 20$.

Mode Marginalization

The above-described implementations can be used to find the best looking pose and shift for an image and reference structure. However, in practice, it is common to marginalize over all poses and shifts, averaging together their contributions weighted by the probability of each pose and shift. Typically only a small number of poses and shifts have significant probability, and they are all concentrated in a mode around the maximally probably r, t.

To support marginalization, the maximally probable pose is first found using the alignment techniques presented in this work. Marginalization is subsequently performed only over poses near to this pose, which provides the benefits of marginalization without the extreme computational cost of current exhaustive approaches.

Use in 2D/2D and 3D/3D alignment

The implementations described above are directed to the alignment of 3D reference structure to a set of 2D images. The approach taught herein, however, can be equally useful when aligning a set of 2D images to a 2D reference. This is often the case in what is known as class averaging or 2D classification. The methods of all the implementations above can be used for 2D-to-2D alignment simply by applying them over a pose space that contains only one dimension of in-plane rotation rather than three dimensions of 3D pose.

Similarly, the methods of all the implementations above can be used for 3D-to-3D alignment simply by applying them over a three dimensional pose space as described above, but applying them over a three dimensional shift space rather than the two dimensions described above.

Use in Heterogeneous Reconstruction

The implementations described above are directed to reconstructing a single 3D structure from a set of 2D images. The approach taught herein, however, can be equally useful when reconstructing multiple structure from a set of images. This is known as heterogeneous reconstruction, or 3D classification. The goal is to separate images into classes, each with a corresponding 3D structure, in order to resolve multiple different structures that may have been simultaneously present in a sample during imaging.

The methods of all of the implementations above can be used for heterogeneous reconstruction by applying them individually to each structure class, and assigning (potentially using soft weights rather than hard assignment) each image to the classes based on the final error E(r,t) for each class. An image will belong with more weight to the classes with lower error.

Use for Added Degrees of Freedom (Advanced Heterogeneity, Flexibility)

Similarly to heterogeneous reconstruction, where an additional degree of freedom is introduced into the problem in the form of class assignment, the methods of the implementations described above can be used in more advanced types of heterogeneity like combinatorial heterogeneity where each image is modeled as a combination of a set of structures, each structure having a binary presence variable. The techniques can also be used when attempting to deal with flexible structures, for instance by parameterizing the flexibility using additional degrees of freedom.

In these cases, the methods of the implementations can be used directly to compute a minimum over the new error function E(r,t,v) where v are the extra degrees of freedom introduced. This can be done by brute force; i.e., by applying the techniques as they are to the new error function, fixing v and repeating for different values of v on a grid over the search space of v. Alternatively the methods of the implementations can be extended by bounding and subdividing over v as well as r and t.

While the above-described embodiments have been described with respect to traditional defocus images from transmission electron microscopes, they can also be applied to phase plates for these microscopes without any modification, requiring only that the correct CTF model be used. The above-described approaches perform well on phase plate data due to the added power at low frequencies.

Although the invention has been described with reference to certain specific embodiments, various modifications thereof will be apparent to those skilled in the art without departing from the spirit and scope of the invention as outlined in the claims appended hereto.

The invention claimed is:

1. A method for image alignment of at least one two-dimensional or three-dimensional image to a two-dimensional or three-dimensional model, executed on a processing unit, the image alignment having an acceptable likelihood of mismatch between the at least one image and the model, the method comprising:

selecting a value for a radius in Fourier space;

discretizing a set of poses into a discrete grid of candidate poses and a set of shifts into a discrete grid of candidate shifts;

determining a fixed fraction ($f_{keep}$) as an upper bound on the acceptable likelihood of mismatch, the fixed fraction being determined based on, at least, the fraction of poses and shifts that are discarded on typical dataset of images;

determining whether a selected accuracy of image alignment has been obtained, when such determination is false:

using the upper bound and a lower bound on the acceptable likelihood of mismatch, the lower bound being a combination of a first component (U(r,t)) and a second component (V(r,t)), the second component comprising a first subcomponent added to a second subcomponent and subtracted by a third subcomponent, the first subcomponent being the power of one of the images at high frequencies, the second subcomponent being the power of an image of a slice of the three-dimensional model for one of the poses at high frequencies, the third subcomponent being the correlation between the power of each of the images at high frequencies and the power of the image of the slice of the three-dimensional model for one of the poses at high frequencies;

determining values for the first component for each of the poses and shifts on the discrete grid of candidate poses and the discrete grid of shifts, using only portions of the image below the selected value for the radius in Fourier space;

determining a reference first component (U*) using the fixed fraction;

for every pose in the discrete grid of candidate poses, determining whether a minimum value of the first component over all the candidate shifts is greater than the reference first component and discarding the pose from the discrete grid in such case;

for every shift in the discrete grid of candidate shifts, determining whether the minimum value of the first component over all candidate poses is greater than the reference first component and discarding the shift from the discrete grid in such case;

for every remaining pose in the discrete grid of candidate poses, replacing the pose with a plurality of subdivided grid points representing the candidate poses;

for every remaining shift in the discrete grid of candidate shifts, replacing the shift with a plurality of subdivided grid points representing the candidate shifts; and increasing the radius in the Fourier space; and otherwise, returning the pose and shift at the lower bound with minimum value.

2. The method of claim 1, wherein the lower bound is determined with the images at a resolution that is less than the maximum resolution for the images.

3. The method of claim 1, wherein the first component is the squared error of Fourier coefficients at or below a selected radius in Fourier space, and the second component is the squared error of Fourier coefficients above the selected radius.

4. The method of claim 1, wherein the second subcomponent comprises:

$$V_1 - \Sigma_{\|l\|>L\frac{1}{2}} C_l^2 |\hat{Y}_l|^2 - 4\sqrt{\Sigma_{\|l\|>L\frac{1}{2}} C_l^2 |\hat{Y}_l|^2},$$

wherein $V_1$ is the power of one of the images at high frequencies, subscript l denotes a wavevector, subscript L denotes the selected radius in the Fourier space, C is a contrast transfer function (CTF) of the image-capturing apparatus, and Y is a vector representing a projection of the three-dimensional model.

5. The method of claim 4, wherein the second subcomponent is only recomputed if the CTF of the image-capturing apparatus is different.

6. The method of claim 1, wherein the determination of the upper bound comprises evaluating a value for the likelihood of mismatch at a specific pose, specific shift, or both.

7. The method of claim 1, wherein determining the reference first component (U*) comprises determining the reference first component (U*) such that:

$$\frac{|\{(r,t); U(r,t) \le U^*\}|}{|\{(r,t); U(r,t) > U^*\}|} = f_{keep}.$$

8. The method of claim 1, wherein the at least one image is two-dimensional and the model is three-dimensional, wherein replacing the pose with the plurality of subdivided grid points comprises replacing the pose with eight subdivided grid points, and wherein replacing the shift with the plurality of subdivided grid points comprises replacing the shift with four subdivided grid points.

9. The method of claim 1, wherein the at least one image is two-dimensional and the model is two-dimensional, wherein replacing the pose with the plurality of subdivided grid points comprises replacing the pose with two subdivided grid points, and wherein replacing the shift with the plurality of subdivided grid points comprises replacing the shift with four subdivided grid points.

10. The method of claim 1, wherein the at least one image is three-dimensional and the model is three-dimensional, wherein replacing the pose with the plurality of subdivided grid points comprises replacing the pose with eight subdivided grid points, and wherein replacing the shift with the plurality of subdivided grid points comprises replacing the shift with eight subdivided grid points.

11. The method of claim 1, wherein the selected accuracy of image alignment is obtained when the value for the radius in Fourier space is equal to the Nyquist rate.

12. The method of claim 1, wherein the selected accuracy of image alignment is obtained when a selected number of iterations have been performed.

13. The method of claim 1, wherein the fixed fraction ($f_{keep}$) is between 3% and 10%.

14. The method of claim 1, wherein the fixed fraction ($f_{keep}$) is approximately 5%.

* * * * *